United States Patent [19]

Snaper

[11] Patent Number: 4,681,541
[45] Date of Patent: Jul. 21, 1987

[54] DENTAL BUR WITH ENHANCED DURABILITY

[76] Inventor: Alvin A. Snaper, 2800 Cameo Cir., Las Vegas, Nev. 89107

[21] Appl. No.: 752,378

[22] Filed: Jul. 5, 1985

[51] Int. Cl.⁴ ............................................. A61C 3/02
[52] U.S. Cl. .................................... 433/165; 408/144
[58] Field of Search ............... 408/144, 145; 407/119; 433/166, 165

[56] References Cited

U.S. PATENT DOCUMENTS 2,084,329 10/1934 Emmons ............................ 407/119
3,755,866 9/1973 Ohlsson ............................. 407/119
4,058,898 11/1977 Nasa ................................... 433/166

Primary Examiner—Robert Peshock
Attorney, Agent, or Firm—Donald D. Mon

[57] ABSTRACT

A dental bur whose abrading or cutting surfaces are covered by an adherent layer of a suitable nitride or carbide deposited thereon. The layer is deposited on edge surfaces and adjacent surfaces by vacuum deposition, are deposition, are catheter sputtering to produce a larger of thickness controlled to be insufficiently thick to form an unsuitably dull edge.

16 Claims, 5 Drawing Figures

U.S. Patent  Jul. 21, 1987  4,681,541
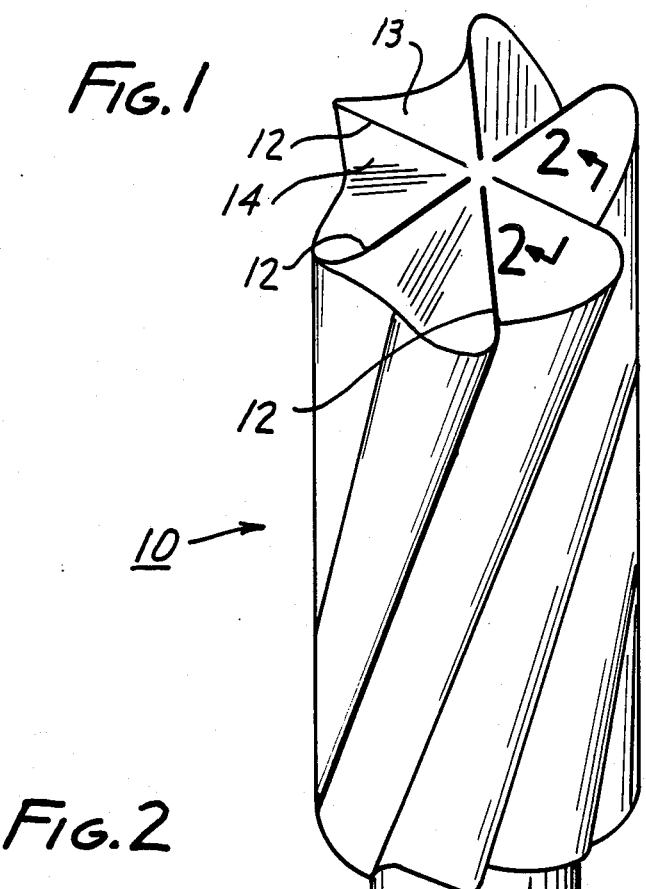
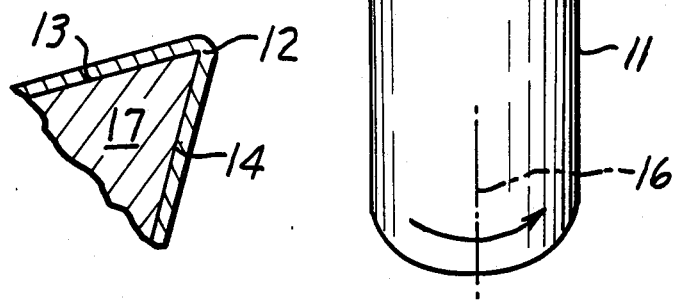
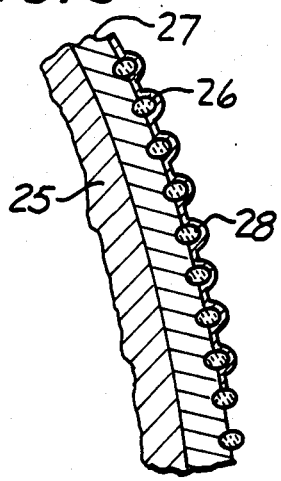
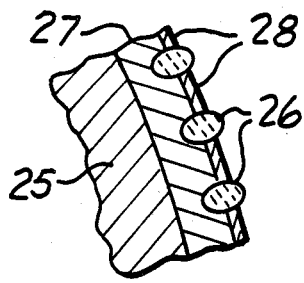
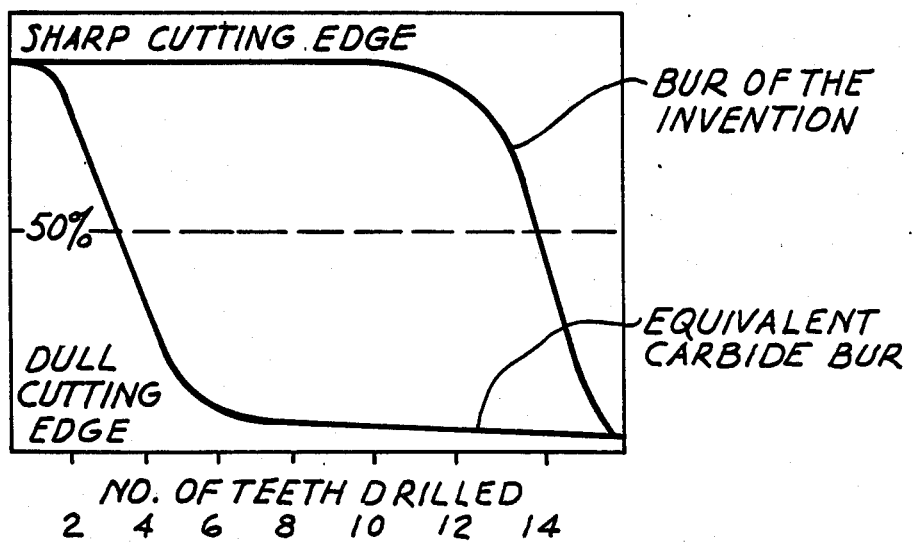

DENTAL BUR WITH ENHANCED DURABILITY

FIELD OF THE INVENTION

This invention relates to dental burs, and in particular to means to enhance their durability and to cause less trauma to the patient.

BACKGROUND OF THE INVENTION

Dental burs are used to drill into teeth, and to shape internal and external tooth surfaces. But their tooth material is hard, and a hard, sharp bur is needed to do the work. In order to do the work with less trauma to the patient, such burs are operated at very high speeds, and particular care is taken with lubrication and cooling. Still, however careful and advanced are the burs and the skills of the dentist, the patient will be traumatized to some extent. Lessening of this tendency requires attention to a variety of causes. While the improvement to each of these causes may individually be very small, the cumulative effect to the patient may be very important.

To the dentist, the cost of burs is important, and the need to change them during a procedure because they become dull is a decided nuisance. The enhancement of durability then has two aspects. One is that a bur which remains sharp longer can in the long run be less traumatic. Another is that a bur which is likelier to remain optimally sharper for a longer period of time and therefore be less expensive.

As a consquence of this invention, drilling and grinding speeds can be shortened, vibration effects from a non-uniformly worn bur can be reduced, and to these improvements can additionally be added improved lubricity and heat transfer properties. A problem that is inherent in conventional efforts to make a sharp and durable bur is that these materials tend to be brittle, and crack and break. Breakage during usage represents a danger to the patient. A piece of the bur may come loose and not be readily retrievable, or may jam in a tooth crevice, requiring sacrifice of some of the tooth. These tendencies may be countered not only by maintaining sharpness longer, but also by providing toughness as well. With conventional burs, these objectives are counter to one another. This invention enables them to be obtained or at least approached at the same time.

While efforts have been made to accomplish the above objectives, the existing bur generally involve composite structures in which cutting bodies are bonded or embedded in a substrate. An example is tungsten carbide cutting inserts bonded to a stainless steel substrate. Such an arrangement provides multiple opportunities for failure.

Optionally an entire bur might be made of tungsten carbide to resist the tendency of the bur to fragment, but this is relativly expensive, and if used should have a means to extend its useful life.

As another example, diamond coated burs have diamond crystals embedded in a relatively soft substrate. When the substrate erodes, the crystals are lost, and the bur no longer functions. Coating a diamond surface to protect the substrate lengthens the life of the bur. It is an object of this invention to provide a more durable dental bur, which can if desired also have improved inherent lubricity and heat conductivity, all to the econonmic benefit of the dentist, and to the reduction of trauma to the patient.

BRIEF DESCRIPTION OF THE INVENTION

According to this invention, a substrate in the form a dental bur with a proper cutting or eroding configuration is coated, at least at its cutting or eroding portions, with a thin layer of a metallic nitride, which nitride is selected for having greater hardness, and perhaps also better lubricity, and heat conductivity than the material of the substrate. The term "reducing" is sometimes used herein generically to describe cutting or abrasion of dental tooth materials. The coating material is applied as an inherently integral layer by means such as vacuum deposition, arc deposition or cathode sputtering, preferably with some tendency, however minor, to diffuse into the substrate. The thickness of the layer is such as not to dull the cutting edges by rounding them excessively when applied to a cutting edge.

According to a preferred but optional feature of the invention, the layer includes a minor amount of dopant such as chromium or vanadium which may enhance a desired property such as hardness, lubricity, or heat conductivity.

The above and other features of this invention will be fully understood from the following detailed description and the accompanying drawings, in which:

BRIEF DESCRIPTION OF THE DRAWINGS

FIG. 1 is a perspective view of a dental bur according to the invention, this being a cutting type bur;

FIG. 2 is a fragmentary cross-section taken at line 2—2 in FIG. 1;

FIG. 3 is a fragmentary cross-sectional view of the eroding surfaces of an eroding type bur;

FIG. 4 is a fragmentary view of a worn bur of the type shown in FIG. 3 and;

FIG. 5 is a schematic showing of some advantages of this bur compared to conventional burs.

DETAILED DESCRIPTION OF THE INVENTION

The presently preferred embodiment of dental bur 10 according to the invention is shown in FIG. 1. It is but one example of a multitude of possible examples. In this example it is an end cutter, and typifies a cutting-type bur. Such dental burs have a shank 11 for insertion into a tool socket, (not shown), and a plurality of cutting edges 12. Each edge is formed to a dihedral angle by a rake surface 13 which provides the usual relief for cutting, and a forward surface 14 which provides for making the sharp edges.

Frequently the elements 12, 13 and 14 are formed as part of a separate body, such as a carbide insert, there being as many of these bodies as there are cutting edges. They are embedded in or bonded to a basic bur body or substrate 15. There are other burs which are unitary, that are not formed by assembly of a plurality of parts, but then every portion of the bur has to have the same physical properties, even though the different parts are used for different purposes, and compromises must be made. This is a matter of indifference to this invention, so that the entire uncoated bur structure is referred to as a "substrate", regardless of how it is manufactured or of how or whether it is assembled. The bur has an axis of rotation 16. According to this invention, and as best shown in FIG. 2, there is formed on the surface of the substrate a hard layer 17. This layer is formed on the substrate by means of a process which forms the layer as a continuation of the substrate surface, and which preferably enables at least some diffusion into the substrate.

The presently preferred techniques are vacuum deposition, cathode sputtering, or arc deposition, in an atmosphere providing carbon or nitrogen which causes a reactive deposition of the carbide or nitride on the substrate.

Metals for the nitride or carbide are selected from the group consisting of titanium, tungsten, and boron. Titanium is preferred, and titanium nitride is the preferred coating.

The process of applying such a coating is well-known, and needs no detailed description here. A clean substrate surface is placed in the coating chamber, and the deposition is begun, gradually depositing material on the substrate. The deposition is stopped when a subitable thickness is formed.

One very useful combination is a substrate made of stainless steel or tool steel with a titanium nitride coating. The coating, which takes the wear is applied to the substrate as before.

Because burs with tungsten carbide inserts are readily available, the layer will frequently be applied to the entire cutting region of such a bur. The nitride is preferred to the carbide, because nitrides are harder and more wear-resistant than carbides. However, deposited carbides may often find useful application on stainless steel substrates, even though nitrides might be still harder.

At the present time it appears to be best practice not to coat the shank of the bur, because this might create some tolerance problems. However, with suitable controls, coating of the entire bur may prove to be more economical in production, and be equally satisfactory in use.

The layer is advantageous over a surprisingly range of large range of thicknesses. Thicknesses as small as 0.5 microns have been found to be useful, although 3.0 microns appears to be optimal. Thicknesses as great as 0.001 inches have proved to be useful, although this approaches the limit where the sharpness of a cutting edge might be unsuitably rounded by the layer at the edge. In the drawings, the thickness of the layer has been greatly exaggerated to illustrate both the layer and this limitation.

Dopants in total quantities, less than about 1% of the total weight of the layer may advantageously be incorporated into the layer as it is formed. Chromium, boron (in titanium nitride or tungsten carbide layers), boron (in tungsten nitride or carbide layers) and vanadium, are examples of dopants which tend to reduce porosity, and improve lubricity and heat transfer.

Speaking generally, it may be said that any nitride layer on a carbide layer will improve the wearability, heat transfer, and lubricity as compared to a carbide layer.

FIG. 5 shows some of the advantages of this invention compared to the prior art. The graph is related to a cutting type bur such as shown in FIG. 1. It relates the cumulative number of teeth worked on, to the remaining sharpness of the cutting edges as grinding proceeds. In the prior art devices, the cutting edge itself is dulled or eroded progressively, and soon its sharpness falls off sharply to an unsatisfactory condition.

Performance above about 50% sharpness is relatively short, and after that it soon becomes a very dull bur. Performance as a sharp edge is very short-lived, and falls off quickly.

FIGS. 3 and 4 show the usefulness of the invention on an eroding type of bur, in this case a diamond-coated bur. In FIG. 3 the substrate comprises a metal base 25, diamond crystals 26, and a matrix 27 in which the diamonds are embedded. This is a conventional diamond bur. Its life is limited by the matrix, because these matrixes are usually relatively soft, such as electroplated nickel. When the matrix erodes, the crystals fall off, and the bur loses it "sharpness", in the sense of efficiency of erosion.

According to this embodiment a layer 28 is applied over the substrate. This layer can be made of any of the materials described for layer 17. It may applied by any of the processes already described.

The diamond crystals are covered, but because the surface is irregular, the layer will soon be eroded through where it coats the diamonds, and the diamonds will then be exposed for erosion of the tooth. However, the matrix between the diamond crystals will be protected by the portions of the layer between the crystals, and the life of this bur will be significantly extended. Also, the lubricity and heat transfer advantages of the layer will be provided.

The term "surface" as used in this embodiment means the exposed parts of the crystals and of the matrix.

Further with respect to cutting type burs, the surfaces and the angle between them can be selected to take advantage of the improved reduction properties of the layer. Therefore the substrate may have different cutting angles and surfaces than if the substrate material itself were to be the cutting agent. These may be appropiate to the material of the layer, and less appropiate to the material of the substrate, but the bur will be improved.

With this invention, the sharpness of the substrate edge is not touched so long as it is covered by the hard layer. Therefore, so long as the hard layer survives, so does optimum sharpness. It should be remembered that the sharpness is determined by the edge of the substrate, and with a suitable thin layer it is not appreciably dulled. Therefore the sharpness of the bur persists for a long time. When the layer is finally heavily eroded, only then does the bur suffer the fate of the uncoated conventional bur, but after the layer is eroded, there still remains the life of the uncoated bur.

The prolongation of sharpness, and the improved reducing properties lead to the advantages described above.

This invention is not to be limited by the embodiments shown in the drawings and described in the description, which are given by way of example and not of limitation, but only in accordance with the scope of the appended claims.

I claim:

1. A dental bur having a substrate which includes surfaces provided as a pair which form an edge to cut dental tooth material which edge is sufficiently hard, and a layer deposited on said edge surfaces and surfaces adjacent to said edge surfaces said layer being formed of a material selected from the groups consisting of nitrides and carbides of titanium and tungsten, said layer being deposited on said edge surfaces and adjacent surfaces by vacuum deposition, arc deposition or cathode sputtering to produce a layer of thickness controlled to be insufficiently thick to form an unsuitably dull edge.

2. A dental bur according to claim 1 in which said layer thickness is controlled to be in the range of 0.5 microns to 1000 microns.

3. A dental bur according to claim 1 in which said controlled thickness is 3.0 microns.

4. A dental bur according to claim 2 in which a minor amount of dopant is deposited in said layer to improve one or more of the following properties of the layer: lubricity, hardness, and heat conductivity.

5. A dental bur according to claim 4 in which said dopant is selected from the group consisting of chromium, tungsten, boron and vanadium, and mixtures of two or more of them.

6. A dental bur according to claim 2 in which said substrate is a homogeneous body.

7. A dental bur according to claim 6 in which said layer is applied as a continuous layer extending between and interconnecting all cutting edges and all said surfaces.

8. A dental bur according to claim 2 in which said substrate comprises a body which carries a plurality of cutting inserts, said edge and surfaces being formed on each said insert.

9. A dental bur according to claim 8 in which said body is steel, and said inserts are silicon carbide.

10. A dental bur according to claim 9 in which said layer is made of titanium nitride.

11. A dental bur according to claim 2 in which said bur has an axis of revolution, and in which a plurality of said cutting edges is formed thereon.

12. A dental bur according to claim 3 in which the angle formed by said surfaces at said edge, and the placement of the edge are optimized to the properties of the layer material.

13. A dental bur according to claim 1 in which said surfaces comprise a metal matrix and diamond crystals imbedded in said matrix, said layer covering the exposed areas of the matrix and the diamond crystals.

14. A dental bur according to claim 13 in which a minor amount of dopant is deposited in said layer to improve one or more of the following properties of the layer: lubricity, hardness, and heat conductivity.

15. A dental bur according to claim 14 in which said dopant is selected from the group consisting of chromium, tungsten, boron and vanadium, and mixtures of two or more of them.

16. A dental bur according to claim 3 in which said substrate is a homogeneous body.

* * * * *

UNITED STATES PATENT AND TRADEMARK OFFICE
CERTIFICATE OF CORRECTION

PATENT NO. : 4,681,541
DATED : July 21, 1987
INVENTOR(S) : Alvin A. Snaper

It is certified that error appears in the above-identified patent and that said Letters Patent are hereby corrected as shown below:

In The Abstract

Line 5, change "are deposition, are catheter" to --arc deposition, or cathode--

Line 6, change "larger" to --layer--

In The Claims

Claim 1, column 4, line 62, change "and" to --or--

Signed and Sealed this

Second Day of February, 1988

Attest:

DONALD J. QUIGG

Attesting Officer    Commissioner of Patents and Trademarks